US00PP08260P

United States Patent [19]

Drewlow

[11] Patent Number: Plant 8,260

[45] Date of Patent: Jun. 15, 1993

[54] POINSETTIA PLANT NAMED FELIZ NAVIDAD

[75] Inventor: Lyndon W. Drewlow, Ashtabula, Ohio

[73] Assignee: Mikkelsens, Inc., Ashtabula, Ohio

[21] Appl. No.: 831,941

[22] Filed: Feb. 6, 1992

[51] Int. Cl.[5] ..... A01H 5/00

[52] U.S. Cl. ..... Plt./86.4

[58] Field of Search ..... Plt./86.4

*Primary Examiner*—James R. Feyrer

*Attorney, Agent, or Firm*—Foley & Lardner

[57] ABSTRACT

A Poinsettia plant names Feliz Navidad, characterized by its bright red bract color, upright growth with strong branching, heavy bract production, large bracts, relatively small cyathia cluster, early flowering under natural short days, and its tolerance to home conditions of low light and high temperatures.

1 Drawing Sheet

The present invention relates to a new and distinctive cultivar of Poinsettia plant, botanically known as *Euphorbia pulcherrima,* and known by the cultivar name Feliz Navidad.

The new cultivar was developed by me through controlled breeding by crossing Mikkelsen Seedling No. 84-651-1 (seed parent) with Mikkelsen Seedling No. 85-982-1 (pollen parent). The selection from the progeny of the cross was identified by No. 86-185-1, and was non-branching and red in flower color. The new non-branching seedling (86-185-1) was then grafted to the excellent branching type cultivar Super Rochford (not patented) in an attempt to transfer the branching habit of Super Rochford to the red seedling. The graft was successful resulting in the seedling having the branching habit of Super Rochford and retaining all other desirable characteristics.

Asexual reproduction by stem cuttings has shown that the unique features of this new Poinsettia are stabilized and are reproduced true to type in successive propagations.

The following characteristics distinguish the new Poinsettia from both its parent cultivars and other cultivated Poinsettia of this type known and used in the floriculture industry:

1. When 5 or more nodes are left after a pinch (apical tip removal) Feliz Navidad will develop full length shoots from each node like Super Rochford and Yuletide (U.S. Plant Pat. No. 7,316) while the original seedling 86-185-1 will develop a full length shoot from only the upper 3 nodes and the balance of shoots are greatly repressed.

2. Feliz Navidad plants at 28 to 30 cm are shorter than the 86-185-1 seedling at 32 to 34 cm when similar size plants are left after pinching, because there is little or no apical dominance in the branched types. Thus, all shoots develop to the same height instead of 3 shoots becoming dominant. Super Rochford is taller at 36 to 38 cm and Yuletide is similar in height.

3. Feliz Navidad has slightly lighter and brighter green leaves than the original seedling 86-185-1, Yuletide and Super Rochford. However, all would be classified as 147A on the R.H.S. Chart.

4. Feliz Navidad is more tolerant to low light levels and high temperature conditions of the average home as its leaves do not yellow and drop like 86-185-1 under these conditions when kept moist, similar to Yuletide and Super Rochford, both of which have excellent foliage retention.

5. Bract coloration of Feliz Navidad is 45B to 45C Red Group which is a lighter red than 86-185-1 (45A to 45B) and Yuletide (between 42A and 45B).

6. Feliz Navidad has a cyathia cluster (flowers in center of bract) that is slightly smaller in number and diameter than the original seedling 86-185-1, and much smaller than Yuletide and Super Rochford.

7. Feliz Navidad is, like 86-185-1, resistant to heat delay of flower bud initiation under night temperatures above 21° C., while Yuletide is slightly susceptible and Super Rochford very susceptible. This is of great commercial importance, especially in the southern U.S.A. and where there are warmer than normal Fall growing months in the north.

8. Bract size of Feliz Navidad is larger (30 to 32 cm) than Yuletide (26 to 28 cm) and Super Rochford (20 to 25 cm). Bract is more reflexed than either Yuletide or Super Rochford. Cyathia will not split apart like Super Rochford but remains in a tight cluster at center of bract like Yuletide.

9. All other characteristics of Feliz Navidad are similar to the original seedling, such as early flowering under natural short days, similar shaped leaves and bracts, retention of cyathia under stress conditions and cyathia that do not split.

The accompanying colored photograph i.e. drawings illustrate a typical plant of Feliz Navidad, with colors being as true as it is reasonably possible to obtain in colored reproductions of this type.

The photograph at the top of the sheet comprises a front perspective view of a typical plant the new cultivar, with the photo being taken on Dec. 19, 1991.

The photograph as the bottom of the sheet comprises a top view of a plant of Feliz Navidad, with the photo being taken on Jul. 11, 1991 under a rigid fiberglass greenhouse covering on an overcast day in Ashtabula, Ohio.

The following detailed description of my new cultivar, based on plants produced in greenhouses in Ashtabula, Ohio during the Fall season of the year. Plants were grown in 15 cm pots and measurements were taken sixteen weeks after rooted cuttings were planted. Height measurements were taken from the soil line of the container. The plants were grown at 64°–68° F. night temperatures under 3500–4000 foot candles of light, and 250 ppm Nitrogen, 75 ppm Potassium, and 250 ppm Phosphorous nutritional levels with trace elements added. Habit of growth, foliage coloration, leaf variegation, size of leaves and flower size will be influenced by nutritional and environmental conditions without, however, any variance in the genotype.

Color references are made to the Royal Horticultural Society Colour Chart except where general terms of ordinary dictionary significance are used.

Parentage: Controlled cross between female Mikkelsen Seedling No. 84-651-1 and male Mikkelsen Seedling No. 85-982-1. The selected seedling was then grafted to a plant of Super Rochford, a branching type plant, to produce the new cultivar, characterized by excellent branching, from the original non-branching seedling.

Propagation

A. *Type cutting.*—Stem 5 to 6 cm long.

B. *Time to root.*—14 days at 21° C. Summer; 18 days at 21° C. Winter.

C. *Rooting habit.*—Abundant, fibrous roots.

Plant Description:

A. *Form.*—Upright; when apical meristem is removed (pinching) leaving 5 or more nodes above soil line to pot, generally all lateral shoots will emerge and develop.

B. *Habit of growth.*—Strong, thick stem holds bracts up for good flower display. Strong branch angle. Bottom stems elongate faster than upper stems, thus producing a semi-upright habit with bract display on upper ⅔ of plant. Growth is vigorous; depending on scheduling system, plants may need an application of a chemical growth regulator such as Cycocel.

C. *Foliage.*—Leaves are alternate and borne on 4.5 to 5.5 cm long petioles reddish purple in color. 1. Size: Mature leaves are 14 to 15 cm long and 10 to 11 cm wide at broadest point near basal areas of plant, with leaves becoming smaller near the bract. 2. Shape: Ovate with acuminate apex and rounded base. 3. Texture: Upper surface glabrous; lower surface glabrous and rugose because of protruding veins. 4. Margin: Entire. 5. Color: Young foliage, top side 146A, under side 146B. Mature foliage, top side 147A, under side 147B.

Flowering description (cyathia):

A. *Flowering habits.*—Earlier flowering than most commercial cultivars, apparently having a longer critical day length for flower initiation. Under controlled daylength, development time is approximately 9 weeks; shows color faster than Yuletide because last 2 or 3 true leaves turn red before bract fully develops, and pollen shed is approximately 1 week earlier than Yuletide. Small cyathia area at center of bract 2 to 3 cm in diameter. Early flower initiation is of commercial significance. Involucre is moderately reflexed.

B. *Natural flowering season.*—November 12 to 22 under Ohio environment.

C. *Cyathia description.*—Stress tolerant, remaining in the involucre for a considerable time under low fertility, low light, high temperature conditions. Severe drying may cause them to drop.

D. *Cyathia borne.*—Closely clustered without growing apart (splitting). Flowering can be initiated any time of the year by controlling the daylength. Cyathia will continue to initiate until daylength is greater than approximately 13 hours.

E. *Quantity of cyathia.*—Highly dependent on cultural practices and can vary from minimum of 2 to 5 to as many as 10 to 15. Cyathia will continue to form from November to April resulting in the large number.

F. *Bracts.*—1. Shape: Ovate (first true bracts) to oblong (later formed bracts); mature bracts (first) 14 to 15 cm long, 8 to 9 cm wide on 2 cm petioles; later bracts 7 to 8 cm long, 3.5 to 4 cm on 1 cm petioles. 2. Color at maturity: Upper surface 45B to 45C.; young bracts are similar in color except they are greenish when very immature; under side 50B with midrib and major veins being greenish in color. 3. Number of bracts: Up to 30 or more depending on growing conditions, with 15 to 20 a normal number; bract size varies with growing conditions, whether plants are pinched and use of growth regulators.

G. *Reproductive organs.*—1. Stamens: numerous. a. Anther shape: oblong, color reddish. b. Filament color: reddish. c. Pollen color: yellow. 2. Pistels: a. Stigma shape: forked, color reddish. b. Style color: reddish. c. Ovaries: 3, celled, size 3 mm, color green when stigma receptive. 3. Nectar cups: 1 nectar cup on each cyathia, with none or 2 occurring rarely; nectar readily available on maturing cyathia.

Disease resistance: Very resistant to botrytis damage on bracts even when bracts are 30 or more days old. Small cyathia area helps prevent botrytis after nectar cups start exuding honey-like substance.

Other important characteristics: Upright growth habit with strong branches combine to hold up large bracts and make sleeving for shipping faster, easier, and without breakage. Early flowering under natural short day conditions eliminates the need for black clothing for mid-November sales.

I claim:

1. A new and distinct cultivar of Poinsettia plant named Feliz Navidad, as illustrated and described.

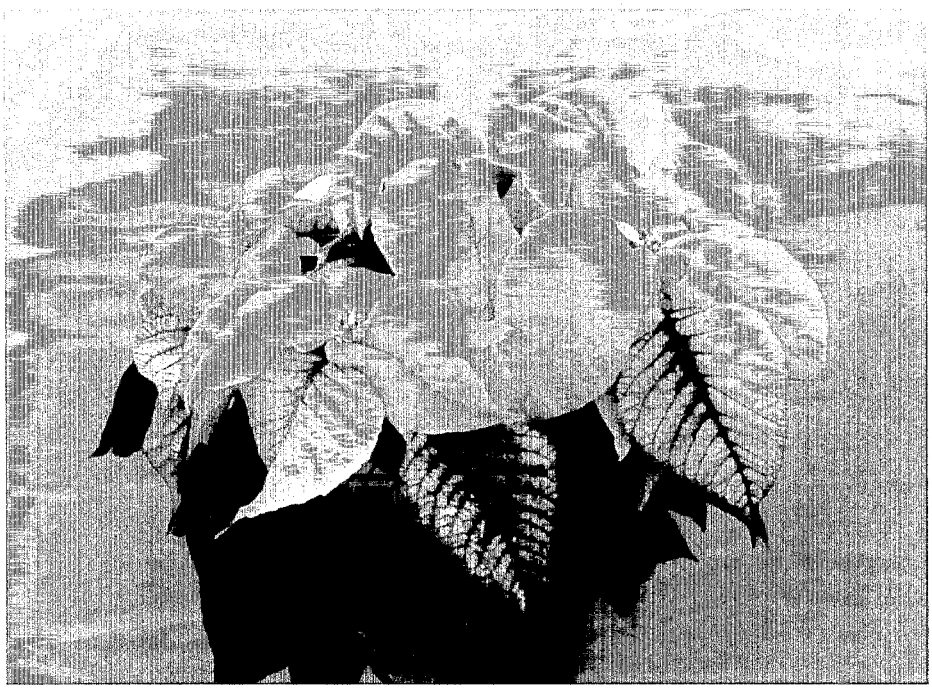
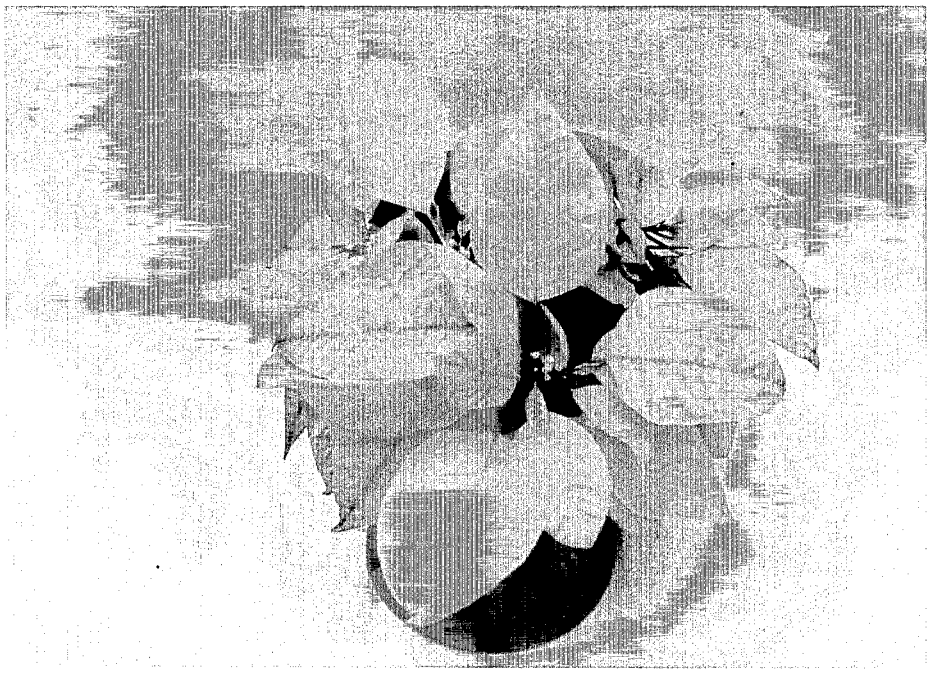

* * * * *